US006949734B2

(12) United States Patent
Neff et al.

(10) Patent No.: US 6,949,734 B2
(45) Date of Patent: Sep. 27, 2005

(54) ACTIVE REMOTE SENSING USING A SPECTRAL LOCK-IN TECHNIQUE

(75) Inventors: Benjamin R. Neff, Fort Wayne, IN (US); Jeff D. Pruitt, Fort Wayne, IN (US); Matthew L. Gypson, Fort Wayne, IN (US); Michael E. Dobbs, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 183 days.

(21) Appl. No.: 10/419,797

(22) Filed: Apr. 22, 2003

(65) Prior Publication Data

US 2004/0212804 A1 Oct. 28, 2004

(51) Int. Cl.[7] .............................. H01J 40/14; H01J 5/16
(52) U.S. Cl. .................... 250/226; 250/214 A; 250/574
(58) Field of Search ............................ 250/226, 214 A, 250/573–575; 327/514; 356/73.1, 340

(56) References Cited

U.S. PATENT DOCUMENTS

| 5,339,155 | A | | 8/1994 | Partridge et al. | |
|---|---|---|---|---|---|
| 6,064,488 | A | * | 5/2000 | Brand et al. | 356/440 |
| 6,473,181 | B1 | * | 10/2002 | Oakberg | 356/365 |
| 6,594,003 | B1 | * | 7/2003 | Horiuchi et al. | 356/73.1 |

OTHER PUBLICATIONS

International Search Report and the Written Opinion of the International Searching Authority of Application No. PCT/US2004/012379 dated Aug. 30, 2004.
M. Dobbs et al., "Validation of Design for Space Based Tunable Diode Laser Absorption Spectroscopy Payload", Proc. Spie—Int. Soc. Opt. Eng. (USA), Proceedings of the Spie—The International Society for Optical Engineering, 2002, Spie–Int. Soc. Opt. Eng., USA, vol. 4817, Jul. 10, 2002, pp. 123–128.

(Continued)

*Primary Examiner*—David Porta
*Assistant Examiner*—Patrick J. Lee
(74) *Attorney, Agent, or Firm*—RatnerPrestia

(57) ABSTRACT

A system for sensing a characteristic of a sample may include a tunable source configured to emit optical radiation that varies over a wavelength range at a first frequency and a reference source configured to emit optical radiation that varies in amplitude at a second frequency. A science detector may be configured to detect the optical radiation from the tunable source and the reference source after interaction with the sample and generate a science signal. A number of lock-in amplifiers may be respectively configured to generate components of the science signal that are present at the first and second frequencies. A processor may be configured to determine a characteristic of the sample based on the components of the science signal that are present at the first and second frequencies.

23 Claims, 6 Drawing Sheets

OTHER PUBLICATIONS

I. Dubinsky et al., "Frequency–Modulation–Enhanced Remote Sensing", Applied Physics B (Lasers and Optics), Oct. 1998, Springer–Verlag, Germany, vol. 867, No. 4, Oct. 1, 1998, pp. 481–492.

Liang–guo Wang "A H/sub 2/0(v) Sensor System for Combustion Diagnostics Using Both Direct Absorption and Frequency Modulation Spectroscopy", New York, NY, USA, IEEE, USA, Oct. 30, 1995, pp. 329–333 vol. 2.

Daniel B. Oh et al., "Frequency Modulation Multiplexing for Simultaneous Detection of Multiple Gases by Use of Wavelength Modulation Spectroscopy with Diode Laswers", Applied Optics, Apr. 20, 1998, Optical Society of America, USA, vol. 37, No. 12, pp. 2499–2501.

A. M. Bullock et al. "Measurement of Absorption Line Wing Structure by Wavelength Modulation Spectroscopy" Applied Physics Letters, American Institute of Physics., New York, US, vol. 70, No. 10, Mar. 10, 1997, pp. 1195–1197.

K. Namjou et al.: "Sensitive absorption spectroscopy with a room–temperature distributed–feedback quantum–cascade laser," Feb. 1, 1998, vol. 23, No. 3, *Optic Letters*, pp. 219–221.

"Alpes Lasers: Applications," http://www.alpeslasers.ch/application/Application.htm, 4 pages.

Co–pending U.S. Appl. No. 10/603,695, entitled, "Active Remote Sensing Using a Simultaneous Spectral Sampling Technique," filed Jun. 26, 2003, 33 page specification and 8 sheets of drawings.

"Application Note 7, FM Spectroscopy With Tunable Diode Lasers," New Focus, San Jose, California, 2001, pp. 1–10.

* cited by examiner

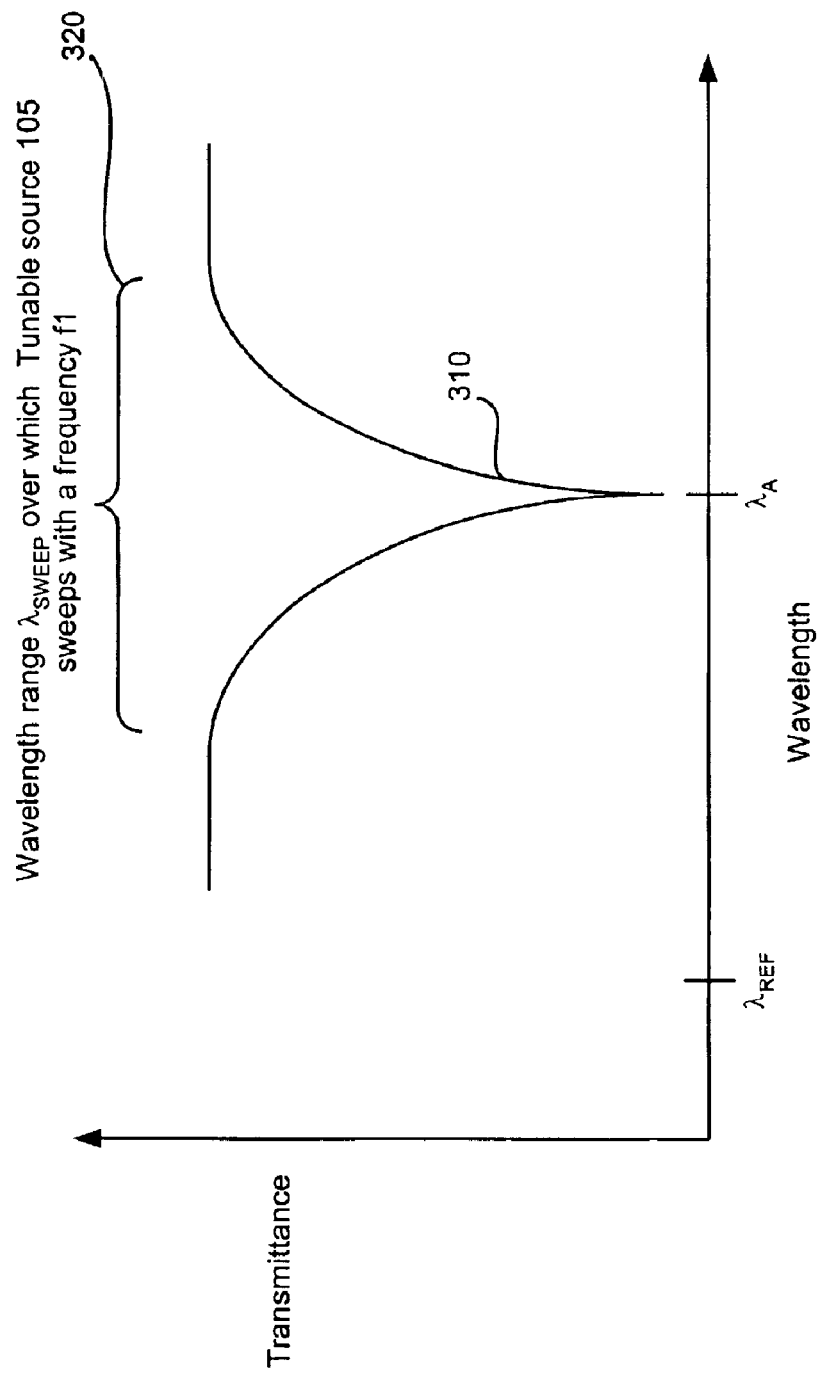

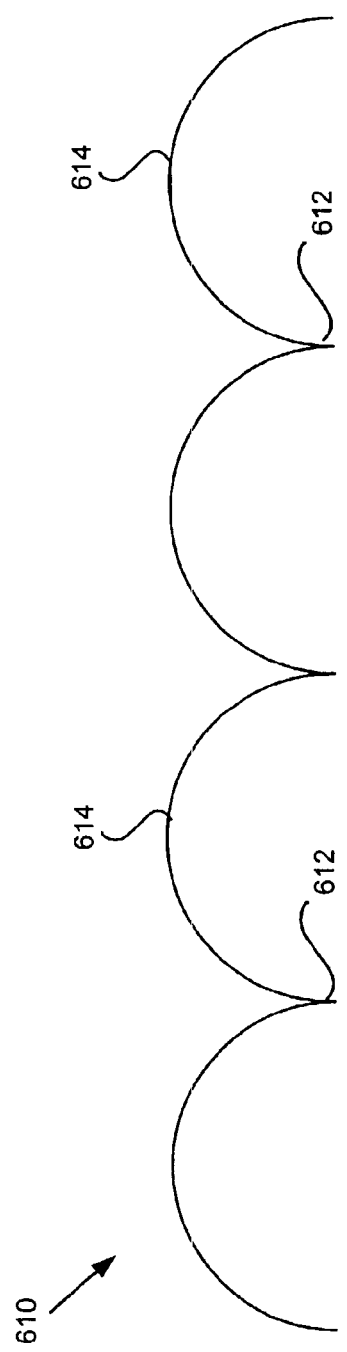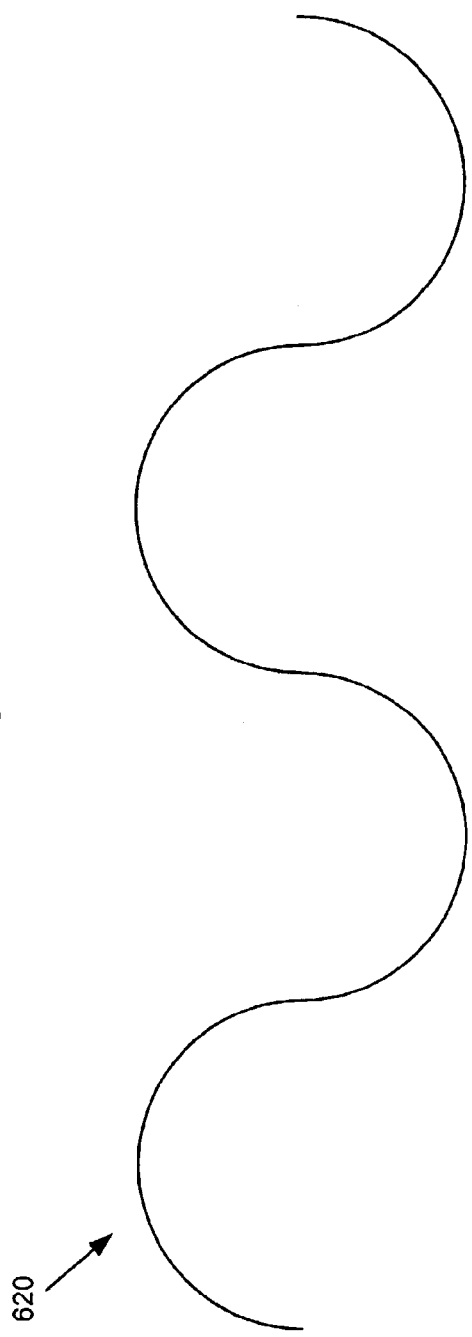

ACTIVE REMOTE SENSING USING A SPECTRAL LOCK-IN TECHNIQUE

BACKGROUND OF THE INVENTION

1. Field of the Invention

This invention relates to remote sensing and, more particularly, to active remote sensing.

2. Description of Related Art

Active remote sensing may be conceptualized as viewing radiation reflected and/or emitted from a certain location in one or more wavelength regions. Active remote sensing typically utilizes one or more sources of radiation (e.g., infrared, visible, or ultraviolet light) to illuminate a target area while measuring the reflected, scattered and/or emitted radiation at one or more detectors. Such remote sensing may be performed from a moving platform or from a stationary location, each of which may be spatially remote from the target area.

One scheme for performing active remote sensing is to stare at an area with a single detector, while illuminating the area with one or more wavelengths of radiation. Various sources of noise, however, may lower the signal-to-noise ratio (SNR) of the measurement. Examples of such noise typically present in active remote sensing include solar background radiation, 1/f noise (i.e., noise whose power varies inversely with frequency), atmospheric turbulence, and/or scintillation.

Thus, there is a need in the art to perform active remote sensing while maintaining a high SNR.

SUMMARY OF THE INVENTION

Systems and processes consistent with the principles of the invention may include, among other things, wavelength modulating one signal at one frequency and amplitude modulating another signal at a different frequency before interaction with a sample of interest. A number of lock-in amplifiers may be used to process radiation detected from the sample at the one frequency and the different frequency.

In accordance with one purpose of the invention as embodied and broadly described herein, a system for sensing a sample may include a first source configured to emit first optical radiation over a range of wavelengths at a first frequency and a second source configured to emit second optical radiation at a predetermined wavelength and that is modulated at a second frequency. A first detector may be configured to detect the first and second optical radiation after interaction with the sample and generate a first detection signal. A first lock-in amplifier may be configured to process the first detection signal based on the first frequency to produce a first output signal. A second lock-in amplifier may be configured to process the first detection signal based on the second frequency to produce a second output signal.

In another implementation consistent with principles of the invention, a method of remotely sensing a sample may include transmitting a beam of optical radiation toward the sample. The beam may include wavelengths periodically varying at a first frequency and an amplitude varying at a second frequency. The method may also include detecting the beam of optical radiation after interaction with the sample to produce a detection signal and determining a portion of the detection signal that is present at the first frequency. The method may include determining another portion of the detection signal that is present at the second frequency and obtaining information about the sample based on the portion of the detection signal and the another portion of the detection signal.

In a further implementation consistent with principles of the invention, a system for sensing a characteristic of a sample may include a tunable source configured to emit optical radiation that varies over a wavelength range at a first frequency and a reference source configured to emit optical radiation that varies in amplitude at a second frequency. A science detector may be configured to detect the optical radiation from the tunable source and the reference source after interaction with the sample and generate a science signal. A number of lock-in amplifiers may be respectively configured to generate components of the science signal that are present at the first and second frequencies. A processor may be configured to determine a characteristic of the sample based on the components of the science signal that are present at the first and second frequencies.

In a yet another implementation consistent with principles of the invention, a method of remotely sensing a target may include generating a first beam of optical radiation that is wavelength modulated at a first frequency and generating a second beam of optical radiation that is amplitude modulated at a second frequency. The first and second beams of optical radiation may be combined for transmission to the target. First and second reference signals at the first and second frequencies may be generated. First radiation and second radiation may be detected from the target using a phase sensitive technique and the first and second reference signals.

BRIEF DESCRIPTION OF THE DRAWINGS

The accompanying drawings, which are incorporated in and constitute a part of this specification, illustrate an embodiment of the invention and, together with the description, explain the invention. In the drawings.

FIG. 3 is a plot illustrating an exemplary spectral feature of interest;

FIGS. 6A and 6B are diagrams illustrating signal conditioning according to an implementation consistent with the principles of the invention.

DETAILED DESCRIPTION

The following detailed description of the invention refers to the accompanying drawings. The same reference numbers may be used in different drawings to identify the same or similar elements. Also, the following detailed description does not limit the invention. Instead, the scope of the invention is defined by the appended claims and equivalents.

As described herein, in one implementation consistent with the principles of the invention, a remote sensing system may wavelength modulate one signal at one frequency and amplitude modulate another signal at a different frequency before interaction with a sample of interest. A number of lock-in amplifiers may be used to process radiation detected from the sample, and perhaps reference radiation, at the one frequency and the different frequency.

Exemplary System

Figure 1:
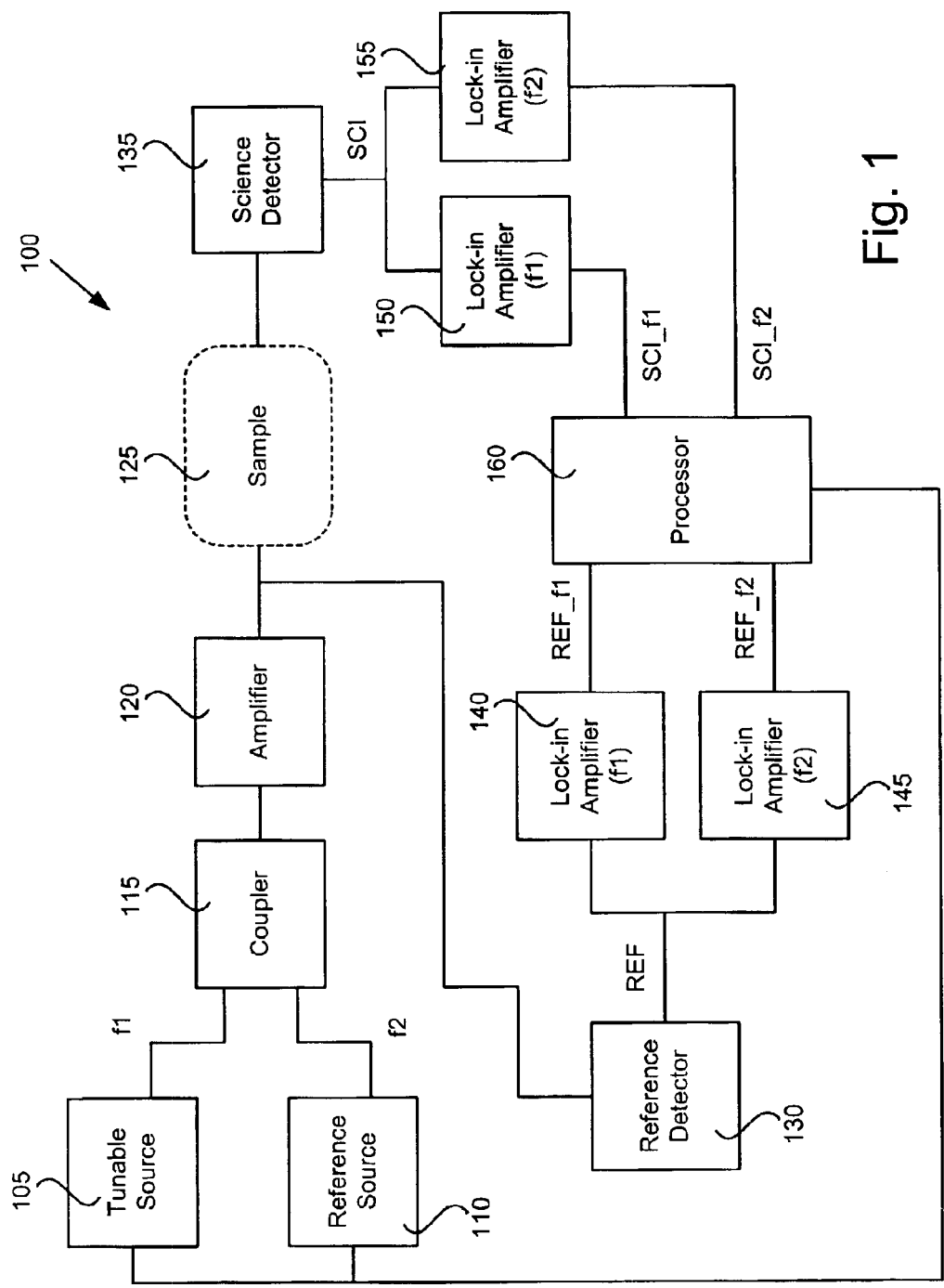
FIG. 1 is a schematic diagram of an active remote sensing system according to an implementation consistent with the principles of the invention.

FIG. 1 is a schematic diagram of an active remote sensing system 100 according to an implementation consistent with the principles of the invention. System 100 may include a tunable source 105, a reference source 110, a coupler 115, an amplifier 120, a sample 125, a reference detector 130, a science detector 135, first through fourth lock-in amplifiers 140/145/150/155, and a processor 160.

Tunable source 105 may include a source of optical or other radiation that is controlled to vary its output. Based on a control signal, tunable source 105 may emit radiation over a range of wavelengths $\lambda_{SWEEP}$. In one implementation consistent with the principles of the invention, tunable source 105 may be configured to continuously vary (or "sweep") its output wavelength over the range $\lambda_{SWEEP}$ at a sweep frequency f1. That is, tunable source 105 may repeat any given wavelength within the range $\lambda_{SWEEP}$ with a period that is the inverse of the sweep frequency f1. One exemplary sweep frequency f1 is about 5 kHz, although this is merely an example and other sweep frequencies may be employed.

Figures 2A, 2B:
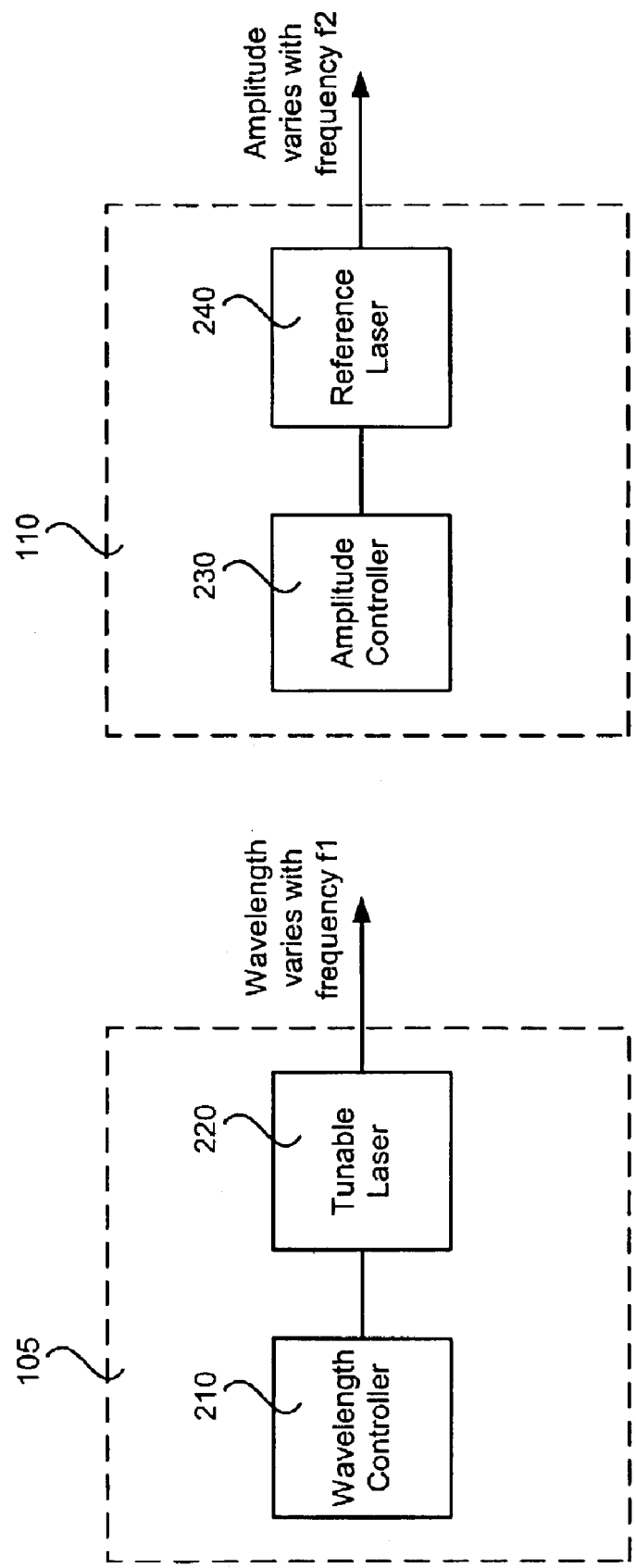
FIG. 2A illustrates an exemplary implementation of a tunable source in the remote sensing system of FIG. 1.
FIG. 2B illustrates an exemplary implementation of a reference source in the remote sensing system of FIG. 1.

FIG. 2A is an exemplary implementation of tunable source 105. Tunable source 105 may include a wavelength controller 210 and a tunable laser 220 whose output is controlled by wavelength controller 210. Wavelength controller 210 may be configured to control the wavelengths produced by tunable laser 220, for example, by varying current that drives tunable laser 220 or the temperature of the tunable laser 220. In turn, wavelength controller 210 may receive feedback signals from tunable laser 220 to aid in its control. Wavelength controller 210 may produce a specific range of wavelengths (e.g., $\lambda_{SWEEP}$) based on input control signals that it receives (e.g., from processor 160).

Tunable laser 220 may include, for example, a distributed feedback (DFB) laser that is precisely tunable in wavelength via a combination of temperature and current. Examples of such tunable lasers 220 include gas, solid, diode, and other types of lasers. Tunable laser 220 may alternately or additionally include a diode laser or an amplified diode laser. The wavelengths of the emitted radiation may fall in the ultraviolet, visible, short-wavelength infrared (SWIR), mid-wavelength infrared (MWIR), long-wavelength infrared (LWIR), or any other electromagnetic region suitable for active remote sensing. Optics (not shown) may be configured to direct the emitted radiation to coupler 115.

The operation of tunable source 105 in FIG. 2A may be further described with respect to FIG. 3. FIG. 3 is a plot of transmittance verses wavelength for an exemplary sample material illustrating an exemplary spectral feature of interest 310. In some implementations, the spectral feature of interest 310 may be an absorption feature and may be associated with a center absorption wavelength $\lambda_A$. Wavelength controller 210 may cause the output wavelength of tunable laser 220 to vary along wavelength range $\lambda_{SWEEP}$ 320 with a sweep frequency f1. Wavelength range $\lambda_{SWEEP}$ 320 may include the entire spectral feature of interest 310 and may extend to wavelengths on either side of spectral feature 310 (or may just extend far enough in wavelength to include spectral feature 310). Those skilled in the remote sensing art will understand how far beyond the spectral region occupied by spectral feature 310 wavelength range $\lambda_{SWEEP}$ 320 may extend.

Returning to FIG. 1, reference source 110 may include a source of optical or other radiation that is controlled to vary its output. Based on a control signal, reference source 110 may emit amplitude-modulated radiation at a reference wavelength $\lambda_{REF}$. In one implementation consistent with the principles of the invention, reference source 110 may be configured to continuously vary the amplitude of its output at a modulation frequency f2. One exemplary modulation frequency f2 is about 7.5 kHz, although this is merely an example and other modulation frequencies may be employed.

FIG. 2B is an exemplary implementation of reference source 110. Reference source 110 may include an amplitude controller 230 and a reference laser 240 whose output is controlled by amplitude controller 230. Amplitude controller 230 may be configured to modulate the signal amplitude produced by reference laser 240, for example, by varying the optical gain of reference laser 240 via an amplitude control signal. In an alternate implementation, amplitude controller 230 may be an optical modulator that acts upon a constant optical output of reference laser 240. Amplitude controller 230 may produce amplitude modulation at a particular modulation frequency f2 based on input control signals that it receives (e.g., from processor 160). In one implementation consistent with the principles of the invention, the modulation frequency f2 of reference source 110 may be different from (and perhaps also not a harmonic of) the sweep frequency f1 of tunable source 105.

The proper choice of values for sweep frequency f1 and modulation frequency f2 may reduce overall noise in system 100. Values for sweep frequency f1 and modulation frequency f2 may also be selected to reduce mutual interference (e.g., inter-modulation). Those skilled in the art will understand in view of this disclosure that frequencies f1 and f2 may be chosen to optimize these and other parameters of system 100.

Reference laser 240 may include, for example, a distributed feedback (DFB) laser that is precisely adjustable in wavelength via a combination of temperature and current. Examples of such reference lasers 240 include gas, solid, diode, and other types of lasers. The wavelengths of the emitted radiation may fall in the ultraviolet, visible, short-wavelength infrared (SWIR), mid-wavelength infrared (MWIR), long-wavelength infrared (LWIR), or any other electromagnetic region suitable for active remote sensing. Optics (not shown) may be configured to direct the emitted radiation from reference laser 240 to coupler 115.

The operation of reference source 110 in FIG. 2B may be further described with respect to FIG. 3. In one implementation consistent with the principles of the invention, the reference wavelength $\lambda_{REF}$ of reference source 110 may fall outside the wavelength range $\lambda_{SWEEP}$ 320 of tunable source 105. In another implementation consistent with the principles of the invention, the reference wavelength $\lambda_{REF}$ of reference source 110 may fall inside the wavelength range $\lambda_{SWEEP}$ 320 of tunable source 105, but away from spectral feature 310.

Returning to FIG. 1, coupler 115 may be configured to combine the output signals from tunable source 105 and reference source 110 into a single output signal. In one implementation consistent with the principles of the invention, coupler 115 may be an optical fiber coupler and may receive the output signals from tunable source 105 and reference source 110 via optical fibers. Although one example of coupler 115 is an optical fiber coupler, those skilled in the art will appreciate that coupler 115 may include any type of optical coupler. Although not strictly necessary for the operation of system 100, coupler 115 may ensure, for example, that the output signals from tunable source 105 and reference source 110 are transmitted with the same optical axis and field of view.

Amplifier 120 may be optionally used after coupler 115. If present, amplifier 120 may be configured to amplify the radiation from coupler 115. In one implementation consistent with the principles of the invention, amplifier 120 may include an erbium-doped fiber amplifier (EDFA) or similar optical amplifier. Although not shown, amplifier 120 may also include one or more of amplifier control circuitry and a beam expander. Those skilled in the art will recognize that various combinations of optical components may be used within amplifier 120 (and/or sources 105/110 and coupler 115) to achieve desired properties of the emitted radiation.

Sample 125 may include a material to be examined by laser spectroscopy. In one implementation, sample 125 may include a cell in, for example, a laboratory environment. In other implementations, sample 125 may include a volume of the atmosphere, which may or may not have a scattering background (e.g., the ground, for a down-looking system 100). Sample 125 may include a solid surface (e.g., the ground), objects (e.g., vehicles), vegetation, chemicals, gas/aerosol, or any other typical target of active remote sensing that has spectral features capable of spectral measurement. Sample 125 may contain a substance having at least one absorption/reflection feature 310 around which tunable source 105 may be swept in wavelength.

The interaction between the output signal from tunable source 105 and sample 125 will now be described. Because the output signal from tunable source 105 is swept repeatedly in wavelength across the range $\lambda_{SWEEP}$ at a sweep frequency f1, its spectral interaction with sample 125 will also repeat at sweep frequency f1. If sample 125 contains spectral feature 310 that absorbs/reflects over the region of interest, a portion of the output signal from tunable source 105 will be absorbed/reflected with a particular temporal pattern. This pattern will repeat at the sweep frequency f1. Hence, sample 125 (and in particular spectral feature 310) may introduce amplitude modulation, repeating at frequency f1, to the output signal from tunable source 105 based on its different absorption/reflection of the signal at different wavelengths.

The interaction between the output signal from reference source 110 and sample 125 will now be described. Because the output signal from reference source 110 is kept at a single reference wavelength $\lambda_{REF}$, its spectral interaction with sample 125 may be considered constant. Thus, unlike the output signal from tunable source 105, the output signal from reference source 110 is not amplitude modulated by sample 125. The output signal from reference source 110, however, may retain its amplitude modulation at modulation frequency f2 when passing through sample 125.

Because the output signal from tunable source 105 and the output signal from reference source 110 are joined by coupler 115, they may experience aspects of system 100 (e.g., amplifier 120) and sample 125 equally. Such common interaction between the signals enables "common mode" rejection of undesired signal perturbations. Any fluctuations unrelated to spectral feature 310 described above will be common to both output signal from tunable source 105 and the output signal from reference source 110. This knowledge may be used to eliminate unwanted fluctuations (i.e., noise) from the desired spectroscopic information about feature 310 in later processing.

After the combination of the output signal from tunable source 105 and the output signal from reference source 110 by coupler 115 (and any amplification by amplifier 120, if present), a small percentage (e.g., about 1%–5%) of the combined signal may be split off and imaged onto reference detector 130. Although not shown in FIG. 1, an optical tap or other suitable optical device may be used for this purpose prior to transmission of the combined signal to sample 125.

Reference detector 130 may be configured to convert an incident optical signal into a corresponding electrical signal, such as a digital signal. Reference detector 130 may include, for example, a high speed (i.e., high bandwidth) photodiode and/or signal conditioning circuitry, such as an analog-to-digital converter (ADC) that digitizes the electrical signal. In one implementation consistent with the principles of the invention, reference detector 130 may digitize the detected signal at a rate above (e.g., 10 times faster than) a desired information rate (e.g., the greater of sweep frequency f1 and modulation frequency f2).

Reference detector 130 may output an electrical, reference signal (REF). Because the REF signal is generated before interaction with sample 125, it may provide a baseline for comparison with another detected signal, as will be understood by those skilled in the remote sensing art.

Science detector 135 may detect optical radiation reflected from or transmitted through sample 125. Science detector 135 may be configured to convert received optical energy into an electrical signal, such as a digital signal, which may be calibrated to correspond to the optical energy of reference detector 130. Similar to reference detector 130, science detector 135 may include a high speed (i.e., high bandwidth) photodiode and/or signal conditioning circuitry.

Science detector 135 may output an electrical, science signal (SCI). Because the SCI signal is generated after interaction with sample 125, it may yield one or more spectral characteristics of sample 125 when processed (e.g., in conjunction with the REF signal), as will be described in greater detail below.

First lock-in amplifier 140 may be configured to receive the REF signal from reference detector 130 and perform "phase-sensitive" detection upon the REF signal at an operational frequency f1. The operational frequency f1 of first lock-in amplifier 140 may be selected to be the same as the sweep frequency f1 of tunable source 105. Those skilled in the electrical arts will be familiar with the operation and construction of lock-in amplifiers (e.g., including tuned filters, mixers, phase shifters, and low pass filters, or similar functions in a digital signal processor (DSP)). In one implementation consistent with the principles of the invention, first lock-in amplifier 140 may operate on a digital REF signal from reference detector 130 via an internal DSP, and may be configured to receive an external reference signal at frequency f1 (not shown) from tunable source 105 or processor 160.

As those skilled in the art will appreciate, the operational/sweep frequency f1 of first lock-in amplifier 140 and tunable source 105 may be selected high enough to significantly reduce 1/f noise that may be present in the radiation emitted by tunable source 105. First lock-in amplifier 140 may output a first signal REF_f1 to processor 160 that corresponds to a portion of the REF signal present at the frequency f1.

Second lock-in amplifier 145 may be configured to receive the REF signal from reference detector 130 and perform "phase-sensitive" detection upon the REF signal at an operational frequency f2. The operational frequency f2 of second lock-in amplifier 145 may be selected to be the same as the modulation frequency f2 of reference source 110. In one implementation consistent with the principles of the invention, second lock-in amplifier 145 may operate on a digital REF signal from reference detector 130 via an internal DSP, and may be configured to receive an external reference signal at frequency f2 (not shown) from reference source 110 or processor 160.

As those skilled in the art will appreciate, the operational/modulation frequency f2 of second lock-in amplifier 145 and reference source 110 may be selected high enough to significantly reduce 1/f noise that may be present in the radiation emitted by reference source 110. Second lock-in amplifier 145 may output a first signal REF_f2 to processor 160 that corresponds to a portion of the REF signal present at the frequency f2.

Third lock-in amplifier 150 and fourth lock-in amplifier 155 may be configured similar to first lock-in amplifier 140 and second lock-in amplifier 145, respectively. Third lock-in amplifier 150 may output a third signal SCI_f1 to processor 160 that corresponds to a portion of the SCI signal output by science detector 135 that is present at the sweep frequency f1. Fourth lock-in amplifier 155 may output a fourth signal SCI_f2 to processor 160 that corresponds to a portion of the SCI signal output by science detector 135 that is present at the modulation frequency f2. Further, a relatively narrow bandwidth about the respective operational frequencies of third and fourth lock-in amplifiers 150/155 may remove a significant amount of noise from sources other than tunable source 105 and reference source 110, such as solar background radiation. Hence, use of third and fourth lock-in amplifiers 150/155 may significantly increase the SNR of the radiation detected by science detector 135.

Figure 4:
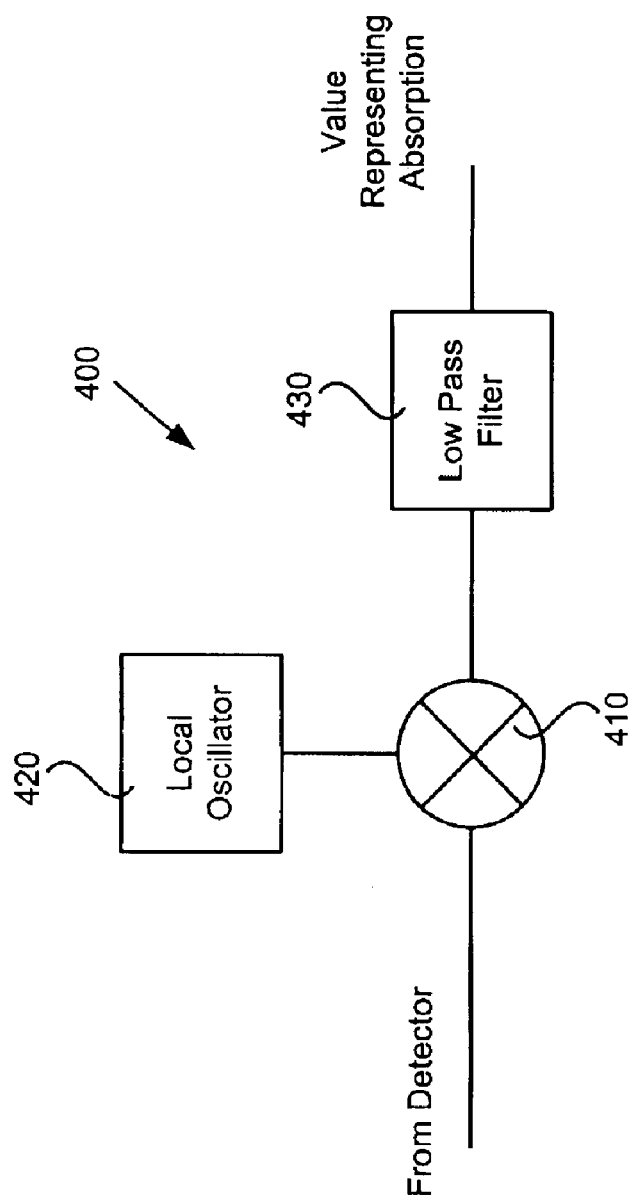
FIG. 4 illustrates an alternate device to replace ones of the lock-in amplifiers in the remote sensing system of FIG. 1.

FIG. 4 is an alternate device 400 that may be used in place of one or more of first through fourth lock-in amplifiers 140/145/150/155 in remote sensing system 100. Device 400 may include a mixer 410, a local oscillator 420, and a low pass filter 430. Mixer 410 may be configured to receive and combine (e.g., by multiplication) a signal from a detector and an output of local oscillator 420. Local oscillator 420 may be configured to generate an output signal that has the same shape as an absorption feature (e.g., spectral feature 310) in the spectral region of interest (e.g., wavelength range $\lambda_{SWEEP}$). It should be noted that the output signal of local oscillator 420 need not have the same shape as the absorption feature. For example, acceptable results may be obtained using a sine wave (e.g., at sweep frequency f1) as the output signal of local oscillator 420. Low pass filter 430 may filter out higher frequencies in the output of mixer 410 to produce a value that represents absorption. Each of mixer 410, local oscillator 420, and low pass filter 430 may be digitally implemented, for example as algorithms within a DSP device.

Returning to FIG. 1, processor 160 may include circuitry to read, format, and/or store data from lock-in amplifiers 140/145/150/155. In one implementation consistent with the principles of the invention, processor 160 stores all data read from lock-in amplifiers 140/145/150/155 for retrieval and processing at a later date. Processor 160 may include one or more shift registers in such an implementation. In other implementations, processor 160 may process the data from lock-in amplifiers 140/145/150/155, rather than merely storing "raw" data. For example, processor 160 may combine REF_f1, REF_f2, SCI_f1, and SCI_f2 from amplifiers 140/145/150/155 to obtain the amount of absorption over the spectral region of interest (e.g., wavelength range $\lambda_{SWEEP}$), as will be described in greater detail below. In other implementations, processor 160 may include a communication link (e.g., a wireless communication link) for transferring raw or processed data from lock-in amplifiers 140/145/150/155 to a remote location.

Processor 160 may also be configured to control the sweep frequency f1 of tunable source 105, and processor 160 may provide an external reference signal at this frequency f1 to first and third lock-in amplifiers 140/150. Similarly, processor 160 may be configured to control the modulation frequency f2 of reference source 110, and processor 160 may provide an external reference signal at this frequency f2 to second and fourth lock-in amplifiers 145/155.

Process of Obtaining Data

Figure 5:
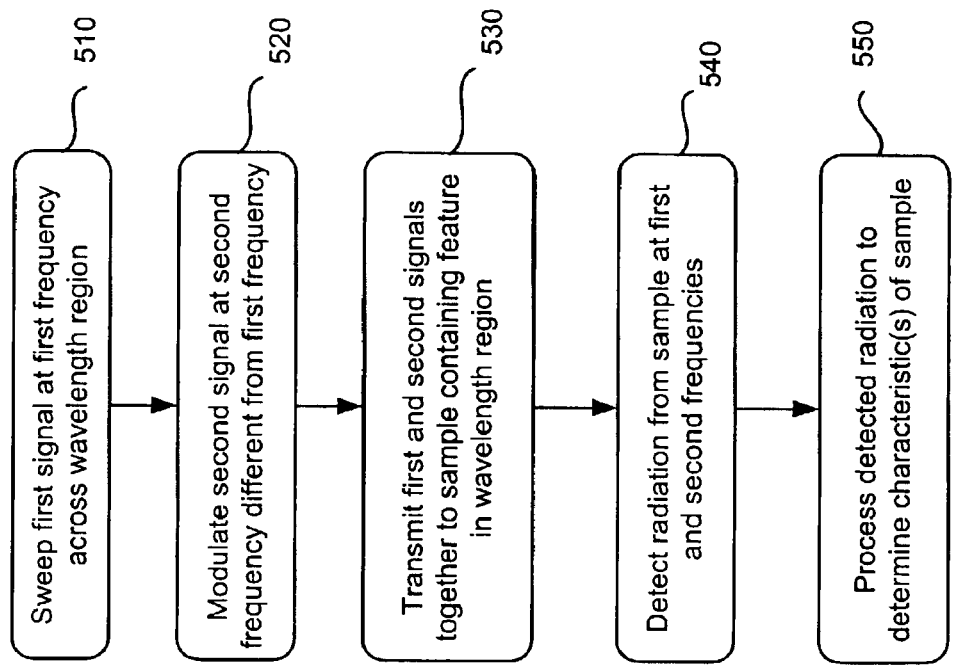
FIG. 5 is flow chart illustrating a process of actively sensing information on a spectral feature within a wavelength range according to an implementation consistent with the present invention.

FIG. 5 is flow chart illustrating a process of actively sensing information on a spectral feature (e.g., spectral feature of interest 310 centered on absorption wavelength $\lambda_A$) within a wavelength range (e.g., $\lambda_{SWEEP}$ 320) according to an implementation consistent with the present invention. The process may begin with tunable source 105 emitting first radiation along the wavelength range $\lambda_{SWEEP}$ [act 510]. In one implementation, tunable source 105 may repeatedly traverse the wavelength range $\lambda_{SWEEP}$ at a first, sweep frequency f1.

Second radiation from reference source 110 may be amplitude modulated at a second, modulation frequency f2 that is different from the first, sweep frequency f1 [act 520]. In one implementation, reference source 110 may emit radiation at a reference wavelength $\lambda_{REF}$ that is outside the wavelength range $\lambda_{SWEEP}$ of the first radiation from tunable source 105.

Processing may continue by transmitting the first and second radiation from tunable source 105 and reference source 110 together to sample 125 [act 530]. In one implementation consistent with the principles of the invention, the first and second radiation may be combined by coupler 115 and optionally amplified by amplifier 120 prior to transmission. Sample 125 may contain a spectral feature of interest 310 within the wavelength range $\lambda_{SWEEP}$ of the first radiation, and this spectral feature 310 may amplitude modulate the first radiation at the first, sweep frequency f1. The second radiation from reference source 110 does not interact with spectral feature 310, and remains amplitude modulated at the second, modulation frequency f2 after interacting with sample 125.

Processing may continue with third and fourth lock-in amplifiers 150/155, in conjunction with science detector 135, respectively detecting radiation from sample 125 at the first frequency f1 and the second frequency f2 [act 540]. Thus, third lock-in amplifier 150 may extract modulation information SCI_f1 at frequency f1 that represents absorption by spectral feature 310. Fourth lock-in amplifier 155 extracts the second, reference signal SCI_f2 that was modulated at frequency f2. In one implementation consistent with the principles of the invention, first and second lock-in amplifiers 140/145, in conjunction with reference detector 130, may respectively detect radiation at the first frequency f1 (i.e., REF_f1) and the second frequency f2 (i.e., REF_f2) before interaction with the sample 125.

The detected radiation SCI_f1 and SCI_f2 (possibly in conjunction with REF_f1 and REF_f2) may be processed by processor 160 to determine characteristics of sample 125 [act 550]. In one implementation, a quantity that is proportional to the area of the spectral feature 310 may be computed as follows:

$$[(SCI\_f1*Ref\_f2)/(SCI\_f2*REF\_f1)]-1 \quad (1)$$

This quantity may be related directly to, for example, a gaseous concentration of sample 125, as will be appreciated by those skilled in the art. This quantity serves to eliminate common mode noise between online and offline channels, and is proportional to the concentration of the absorbing medium (e.g., sample 125). It has been normalized to facilitate comparison between different configurations of this implementation.

The above-described spectral lock-in technique uses lock-in signal recovery techniques to perform spectral sensing, such as total column gas concentration retrieval. This technique permits real time processing and very high data rates. Advantageously, the above-described scheme may be performed very quickly, which may improve the measurement SNR relative to other methods of gathering spectral data.

Exemplary Signal Conditioning

FIGS. 6A and 6B are diagrams illustrating signal conditioning in system 100 according to an implementation consistent with the principles of the invention. Signal 610 in FIG. 6A may be one example of science signal SCI produced by science detector 135. As has been described, signal 610 may vary periodically based on, for example, absorption by spectral feature 310 in sample 125. Depending on the "shape" (in the wavelength region) of spectral feature 310, "sharp" peaks 612 or "blunt" peaks 614 in signal 610 may correspond to spectral feature 310. Regardless of which peak 612/614 in signal corresponds to spectral feature, however, lock-in amplifiers 150/155 may not perform optimally on signal 610, because of the harmonics therein due to the abrupt transitions of sharp peaks 612.

Accordingly, signal 610 may be conditioned (e.g., by circuitry in science detector 135 or by other conditioning circuitry, not shown) to produce conditioned signal 620 in FIG. 6B. For example, alternating periods of signal 610 may be inverted between peaks 612 to produce conditioned signal 620. Those skilled in the art will understand signal conditioning circuitry that may remove harmonics in signal 610 to produce conditioned signal 620 without undue experimentation. Conditioned signal 620 may be input to lock-in amplifiers 150/155, which may perform more optimally on this conditioned signal, thereby improving the performance of system 100.

Conclusion

Systems and methods consistent with the principles of the invention may wavelength modulate one signal at one frequency and amplitude modulate another signal at a different frequency before interaction with a sample of interest. A number of phase sensitive devices may be used to process radiation detected from the sample at the one frequency and the different frequency.

The foregoing description of preferred embodiments of the present invention provides illustration and description, but is not intended to be exhaustive or to limit the invention to the precise form disclosed. Modifications and variations are possible in light of the above teachings or may be acquired from practice of the invention. For example, "multispectral" data may be collected at two or more different wavelengths consistent with the principles of the invention. Further, it is specifically contemplated that "multispectral" may include tens to hundreds of wavelengths (i.e., hyperspectral), to thousands of different wavelengths (e.g., ultraspectral).

Further, additional channels may be used in system 100. For example, one or more additional swept laser, detector, and lock-in amplifier configurations may be added to sweep (in wavelength) one or more additional features of interest within sample 125. Hence, system 100 is not limited to the exact number of sources and detectors illustrated in FIG. 1, as will be understood by those skilled in the art in view of this disclosure.

Also, the phase sensitive detection technique described herein may be used in multiple sensing scenarios. For example, it may be used to: probe areas or materials for concentrations of certain chemicals; determine the presence of harmful chemicals in civilian areas; monitor environmental processes; monitor industrial processes; monitor industrial environments; find and track chemicals in air/water; provide early warning of threats; and/or any other detection scenario that those skilled in the art may envision involving one or more spectral features of interest.

Moreover, the acts in FIG. 5 need not be implemented in the order shown; nor do all of the acts need to be performed. Also, those acts which are not dependent on other acts may be performed in parallel with the other acts. Further, the acts in these figures may be implemented as instructions, or groups of instructions, in a computer-readable medium.

No element, act, or instruction used in the description of the present application should be construed as critical or essential to the invention unless explicitly described as such. Also, as used herein, the article "a" is intended to include one or more items. Where only one item is intended, the term "one" or similar language is used. The scope of the invention is defined by the claims and their equivalents.

What is claimed:

1. A system for sensing a sample, comprising:
   a first tunable source configured to emit first optical radiation over a range of wavelengths that is swept at a first frequency;
   a second fixed source configured to emit second optical radiation at a predetermined fixed wavelength that is amplitude modulated at a second frequency, the first tunable source and the second fixed source emitted simultaneously;
   a first detector configured to detect the first and second optical radiation scattered/reflected from the sample and generate a first detection signal;
   a first lock-in amplifier configured to process the first detection signal based on the first frequency to produce a first output signal; and
   a second lock-in amplifier configured to process the first detection signal based on the second frequency to produce a second output signal,
   wherein the first and second frequencies are not harmonically related to each other and are preselected to reduce inter-modulation between each other.

2. The system of claim 1, further comprising:
   a coupler connected to the first source and the second source and configured to combine the first optical radiation and the second optical radiation into a combined signal; and
   an optical amplifier connected to the coupler and configured to amplify the combined signal.

3. The system of claim 1, further comprising:
   a second detector configured to detect the first and second optical radiation before interaction with the sample and generate a second detection signal;
   a third lock-in amplifier configured to process the second detection signal based on the first frequency to produce a third output signal; and a fourth lock-in amplifier configured to process the second detection signal based on the second frequency to produce a fourth output signal.

4. The system of claim 3, wherein the sample includes a spectral feature within the range of wavelengths, the system further comprising:
a processor configured to process the first output signal, the second output signal, the third output signal, and the fourth output signal to obtain information relating to the spectral feature.

5. The system of claim 4, wherein the information includes a concentration of the sample.

6. The system of claim 1, wherein
the system is disposed in an aircraft or a satellite for remotely sensing the sample.

7. A method of remotely sensing a sample, comprising:
transmitting a beam of optical radiation toward the sample, the beam including a first tunable source that is swept over a range or wavelengths periodically varying at a first frequency and a second fixed source at a predetermined fixed wavelength that is amplitude modulated at an amplitude varying at a second frequency, the first tunable source and the second fixed source transmitted simultaneously;
detecting the beam of optical radiation after scattering/reflection from the sample to produce a detection signal;
determining a portion of the detection signal that is present at the first frequency;
determining another portion of the detection signal that is present at the second frequency; and
obtaining information about the sample based on the portion of the detection signal and the another portion of the detection signal,
wherein the first and second frequencies are not harmonically related to each other and are preselected to reduce inter-modulation between each other.

8. The method of claim 7, further comprising:
generating a tuning signal that periodically varies over the wavelengths at the first frequency;
generating a reference signal that is amplitude modulated at the second frequency; and
combining the tuning signal and the reference signal into the beam of optical radiation.

9. The method of claim 8, further comprising:
amplifying the beam of optical radiation before the transmitting.

10. The method of claim 7, wherein the determining a portion of the detection signal uses a lock-in technique and an external reference signal at the first frequency, and
wherein the determining another portion of the detection signal uses the lock-in technique and another external reference signal at the second frequency.

11. The method of claim 7, wherein the information about the sample includes an area of a spectral feature of the sample.

12. A system for sensing a characteristic of a sample, comprising:
a tunable source configured to emit optical radiation that varies over a wavelength range at a first frequency;
a reference source configured to emit optical radiation at a predetermined fixed wavelength that varies in amplitude at a second frequency, the tunable source and the reference source emitted simultaneously;
a science detector configured to detect the optical radiation from the tunable source and the reference source after scattering/reflection from the sample and generate a science signal;
a plurality of lock-in amplifiers respectively configured to generate components of the science signal that are present at the first and second frequencies; and
a processor configured to determine a characteristic of the sample based on the components of the science signal that are present at the first and second frequencies,
wherein the first and second frequencies are not harmonically related to each other and are preselected to reduce inter-modulation between each other.

13. The system of claim 12, further comprising:
a coupler configured to combine the optical radiation from the tunable source and the reference source into a combined signal.

14. The system of claim 12, further comprising:
an optical amplifier connected to the coupler and configured to amplify the combined signal and transmit the combined signal toward the sample.

15. The system of claim 12, further comprising:
a reference detector configured to detect the optical radiation from the tunable source and the reference source before scattering/reflection from the sample and generate a reference signal;
a second plurality of lock-in amplifiers respectively configured to generate components of the reference signal that are present at the first and second frequencies.

16. The system of claim 15, wherein the processor is further configured to determine the characteristic of the sample based on the components of the reference signal that are present at the first and second frequencies.

17. The system of claim 12, wherein the characteristic includes a concentration of the sample.

18. A method of remotely sensing a target, comprising:
generating a first beam of optical radiation that is wavelength modulated at a first frequency;
generating a second beam of optical radiation that is amplitude modulated at a second frequency, wherein the first and second frequencies are not harmonically related to each other and are preselected to reduce inter-modulation between each other;
combining the first and second beams of optical radiation for transmission to the target;
generating first and second reference signals at the first and second frequencies; and
detecting first radiation and second radiation scattered/reflected from the target using a phase sensitive technique and the first and second reference signals.

19. The method of claim 18, wherein the first beam of radiation varies over a predetermined range of wavelengths, and
wherein the second beam of radiation has a reference wavelength that falls outside the predetermined range of wavelengths.

20. The method of claim 18, further comprising:
amplifying the first and second beams of optical radiation after the combining.

21. The method of claim 18, further comprising:
detecting third radiation and fourth radiation before scattering/reflection from the target using the phase sensitive technique and the first and second reference signals.

22. The method of claim 21, further comprising:
determining one or more characteristics of the target based on the first radiation, the second radiation, the third radiation, and the fourth radiation.

23. The method of claim 18, wherein
generating and combining the first and second beams are performed in an aircraft or a satellite.

* * * * *